US011369264B2

(12) United States Patent
Yokoi et al.

(10) Patent No.: US 11,369,264 B2
(45) Date of Patent: Jun. 28, 2022

(54) METHOD FOR DYNAMIC EVALUATION OF TEAR FLUID LAYER AND DEVICE THEREFOR

(71) Applicants: KYOTO PREFECTURAL PUBLIC UNIVERSITY CORPORATION, Kyoto (JP); KOWA COMPANY, LTD., Nagoya (JP)

(72) Inventors: Norihiko Yokoi, Kyoto (JP); Yuka Sugiura, Higashimurayama (JP); Katsumi Yabusaki, Higashimurayama (JP)

(73) Assignees: KYOTO PREFECTURAL PUBLIC UNIVERSITY CORPORATION, Kyoto (JP); KOWA COMPANY, LTD., Aichi (JP)

( * ) Notice: Subject to any disclaimer, the term of this patent is extended or adjusted under 35 U.S.C. 154(b) by 114 days.

(21) Appl. No.: 16/637,210

(22) PCT Filed: Aug. 9, 2018

(86) PCT No.: PCT/JP2018/029860
§ 371 (c)(1),
(2) Date: Feb. 6, 2020

(87) PCT Pub. No.: WO2019/031569
PCT Pub. Date: Feb. 14, 2019

(65) Prior Publication Data
US 2020/0367743 A1 Nov. 26, 2020

(30) Foreign Application Priority Data
Aug. 10, 2017 (JP) .............................. JP2017-155026

(51) Int. Cl.
*A61B 3/10* (2006.01)
*G06T 7/136* (2017.01)
(Continued)

(52) U.S. Cl.
CPC ............ *A61B 3/101* (2013.01); *G06T 7/0012* (2013.01); *G06T 7/13* (2017.01); *G06T 7/136* (2017.01); *G06T 2207/30041* (2013.01)

(58) Field of Classification Search
CPC ........... A61B 3/101; G06T 7/136; G06T 7/13; G06T 7/0012; G06T 2207/30041
See application file for complete search history.

(56) References Cited

U.S. PATENT DOCUMENTS 8,256,898 B2  9/2012  Gratton et al.
8,909,327 B1  12/2014  Bosworth
(Continued)

FOREIGN PATENT DOCUMENTS

JP   2000-254099 A   9/2000
JP   2001-309889 A   11/2001
(Continued)

OTHER PUBLICATIONS

Remeseiro et al. "CASDES: A Computer-Aided System to Support Dry Eye Diagnosis Based on Tear Film Maps." IEEE Journal of Biomedical and Health Informatics, vol. 20, No. 3, May 2016, pp. 936-943 (Year: 2016).*
(Continued)

*Primary Examiner* — Jon Chang
(74) *Attorney, Agent, or Firm* — McDermott Will & Emery LLP

(57) ABSTRACT

A method for dynamically evaluating a tear fluid layer using an interference fringe image of the tear fluid layer composed of a plurality of consecutive frames, and includes: an image creation step of creating at least one break detection image of a first break detection image, a second break detection image, a third break detection image, and a fourth break detection image, which are images for detecting a breaking site of the tear fluid layer; a determination step of determining whether the break detection image created by the image creation step corresponds to a predetermined breakup pattern; a tally step of tallying the determination results determined by the determination step; and an evaluation step of evaluating, on the basis of a tallied result by the tally step, (Continued)

a breakup pattern of the interference fringe image of the tear fluid layer.

17 Claims, 12 Drawing Sheets

(51) Int. Cl.
*G06T 7/13* (2017.01)
*G06T 7/00* (2017.01)

(56) References Cited

U.S. PATENT DOCUMENTS

| 9,028,065 | B2 | 5/2015 | Yokoi et al. | |
|---|---|---|---|---|
| 2006/0197990 | A1 | 9/2006 | Myodo et al. | |
| 2012/0300174 | A1 | 11/2012 | Yokoi et al. | |
| 2020/0074627 | A1* | 3/2020 | Yokoi | A61B 3/101 |
| 2020/0154995 | A1* | 5/2020 | Yabusaki | A61B 3/14 |

FOREIGN PATENT DOCUMENTS

| JP | 2005211173 | A | * | 8/2005 | A61B 3/145 |
|---|---|---|---|---|---|
| JP | 2011-156030 | A | | 8/2011 | |
| JP | 2017-136212 | A | | 8/2017 | |
| WO | 2015/073986 | A1 | | 5/2015 | |

OTHER PUBLICATIONS

Khamene et al. "A Spectral-Discrimination Method for Tear-Film Lipid-Layer Thickness Estimation from Fringe Pattern Images." IEEE Transactions on Biomedical Engineering, vol. 47, No. 2, Jan. 2000, pp. 249-258 (Year: 2000).*

Alonso-Caneiro et al. "Assessment of Tear Film Surface Quality Using Dynamic-Area High-Speed Videokeratoscopy." IEEE Transactions on Biomedical Engineering, vol. 56, No. 5, May 2009, pp. 1473-1481 (Year: 2009).*

Extended European Search Report issued in European Patent Application No. 18844150.5, dated Mar. 25, 2021.

Yokoi, Norihiko et al., "Tear film change and image analysis: current status and issues," Journal of Japan Ophthalmologists Association; Apr. 20, 2015, vol. 86 No. 4, pp. 21-26, with partial English translation.

Yokoi, Norihiko et al., "Tear film change and image analysis: current status and issues," Journal of Japan Ophthalmologists Association; Apr. 20, 2015, vol. 86 No. 4, pp. 21-26, non-official translation.

Szczesna, D. H. et al., "Interferometric measurements of dynamic changes of tear film", J Biomed Opt, 2006, vol. 11, No. 3, 034028.

International Search Report and Written Opinion issued in International Patent Application No. PCT/JP2018/029860, dated Sep. 25, 2018; with partial English translation.

* cited by examiner

[FIG. 1]

| NAME | Area break | Line break | Dimple break | Spot break |
|---|---|---|---|---|
| IMAGE | | | | |
| TIMING | DURING EYE OPENING | AFTER EYE OPENING (DURING SPREADING OF OIL LAYER) | AFTER EYE OPENING (DURING SPREADING OF OIL LAYER) | DURING EYE OPENING |
| LOCATION | WIDE RANGE OF CORNEA | LOWER PART OF CORNEA | CENTER PART OF CORNEA | CENTER TO UPPER PART |
| CHARACTERISTIC | NO OIL LAYER SPREADING | LINEAR | SUBSTANTIALLY LINEAR | SUBSTANTIALLY CIRCULAR SHAPE |
| TYPE | AQUEOUS TEAR DEFICIENT TYPE (SEVERE) | AQUEOUS TEAR DEFICIENT TYPE | SHORT BUT TYPE (DECREASED WETTABILITY TYPE) | SHORT BUT TYPE |
| CAUSE | SEVERE MOISTURE DEFICIENCY | SLIGHT TO MEDIUM MOISTURE EFICIENCY | DECREASED WETTABILITY IN CORNEA | DECREASED WETTABILITY IN CORNEA |

[FIG. 2]

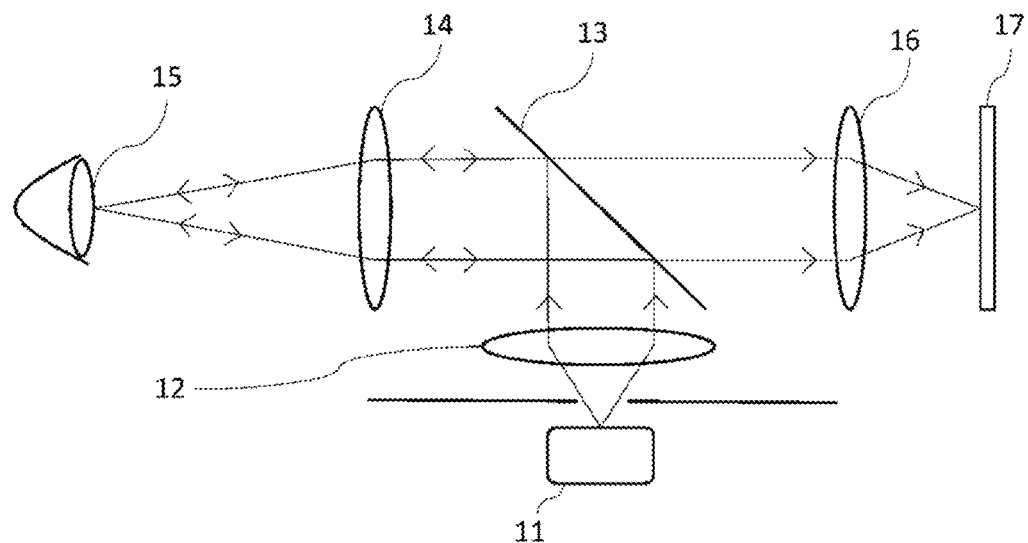

[FIG. 3]
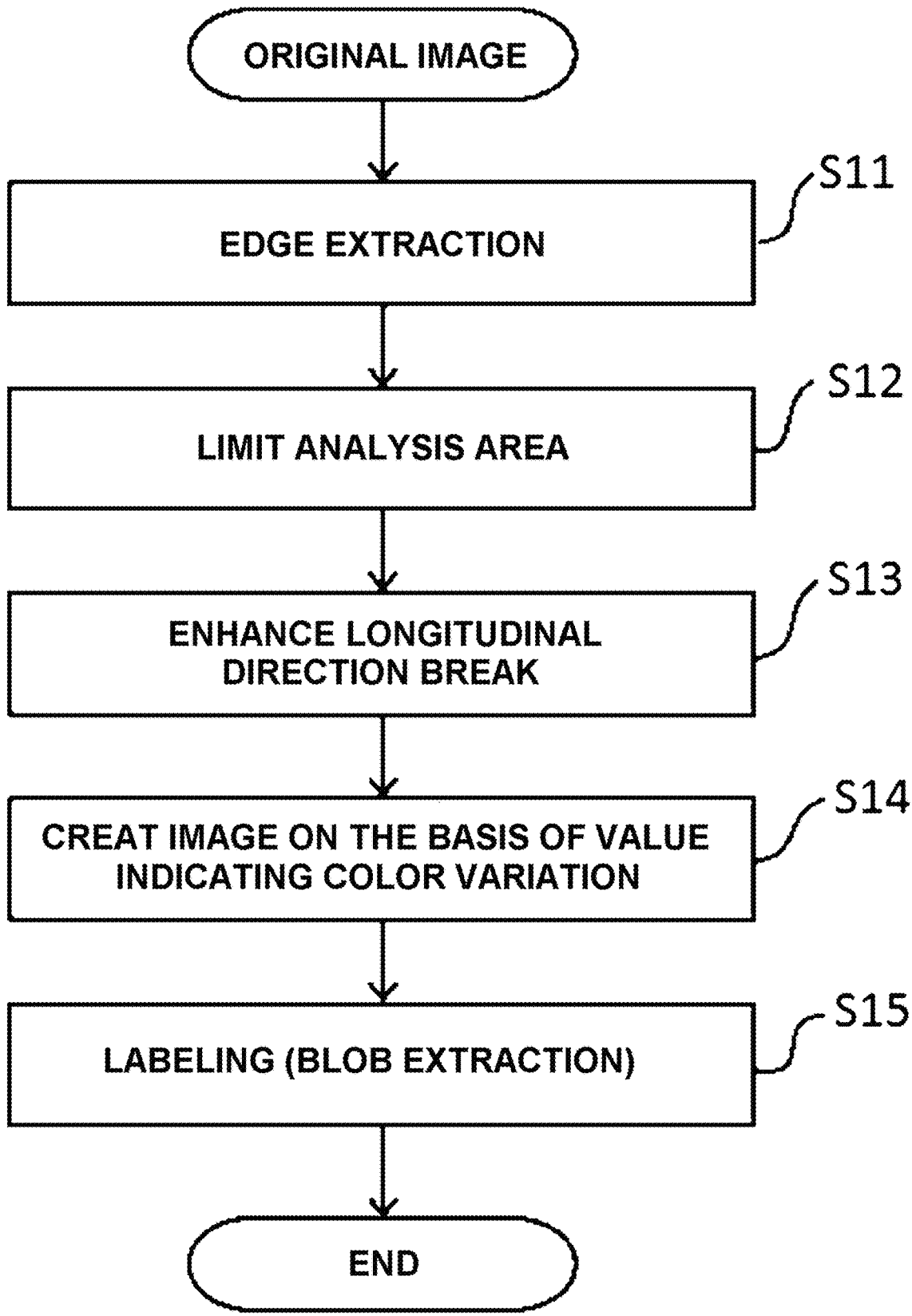

[FIG. 4]
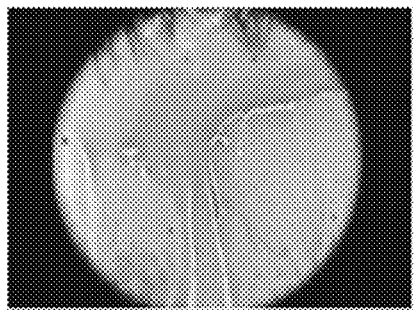
(A)
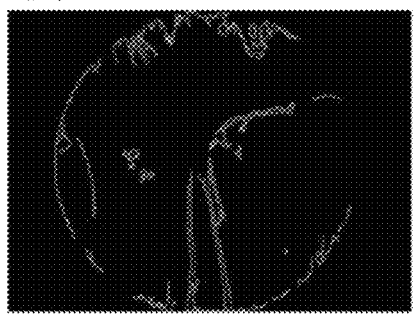
(B)
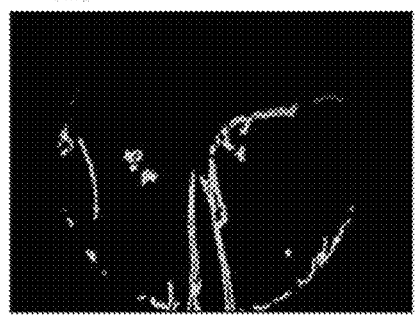
(E)
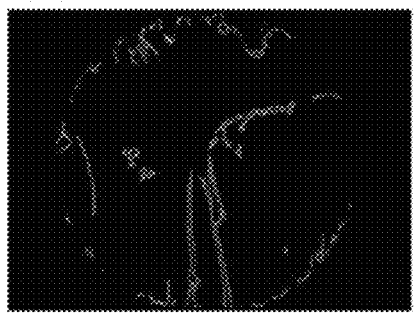
(C)
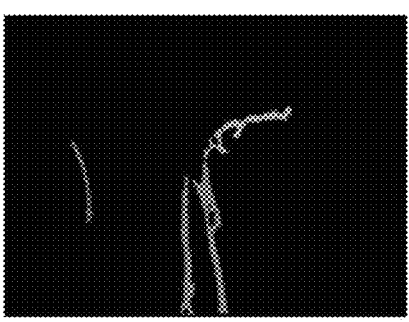
(F)
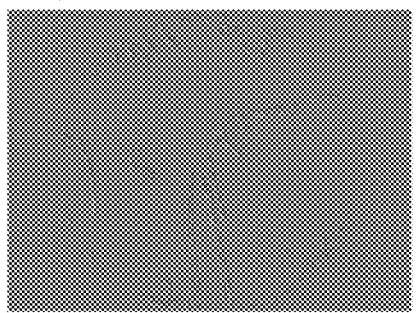
(D)

[FIG. 5]

A REGION 1 / PIXEL OF INTEREST 1

| 155 | 152 | 152 | 156 | 155 | 154 | 152 | 151 |
|---|---|---|---|---|---|---|---|
| 155 | 154 | 151 | 158 | 153 | 159 | 158 | 152 |
| 156 | 158 | 153 | 157 | 157 | 156 | 151 | 153 |
| 153 | 151 | 158 | 153 | 152 | 151 | 154 | 156 |
| 158 | 151 | 152 | 158 | 143 | 144 | 151 | 156 |
| 155 | 153 | 158 | 151 | 141 | 145 | 159 | 157 |
| 153 | 151 | 159 | 158 | 156 | 157 | 156 | 155 |
| 159 | 153 | 154 | 152 | 153 | 155 | 152 | 156 |

PIXEL OF INTEREST 2
REGION 2

B

| 1.4 | 1.7 | 2.7 | 2.6 | 2.3 | 2.8 | 3.4 | 3.2 |
|---|---|---|---|---|---|---|---|
| 2.0 | 2.2 | 2.7 | 2.5 | 1.9 | 2.7 | 3.0 | 2.6 |
| 2.4 | 2.6 | 3.0 | 2.8 | 2.9 | 3.0 | 3.0 | 2.6 |
| 3.3 | 3.0 | 3.1 | 4.7 | 5.6 | 4.8 | 3.8 | 2.3 |
| 2.7 | 3.0 | 3.2 | 6.2 | 5.6 | 5.9 | 5.3 | 2.7 |
| 2.7 | 3.2 | 3.6 | 6.8 | 7.1 | 7.0 | 5.5 | 2.7 |
| 2.8 | 3.0 | 3.2 | 5.5 | 5.7 | 5.9 | 4.1 | 2.3 |
| 3.5 | 3.4 | 3.3 | 2.8 | 2.3 | 1.9 | 1.7 | 1.9 |

[FIG. 6]
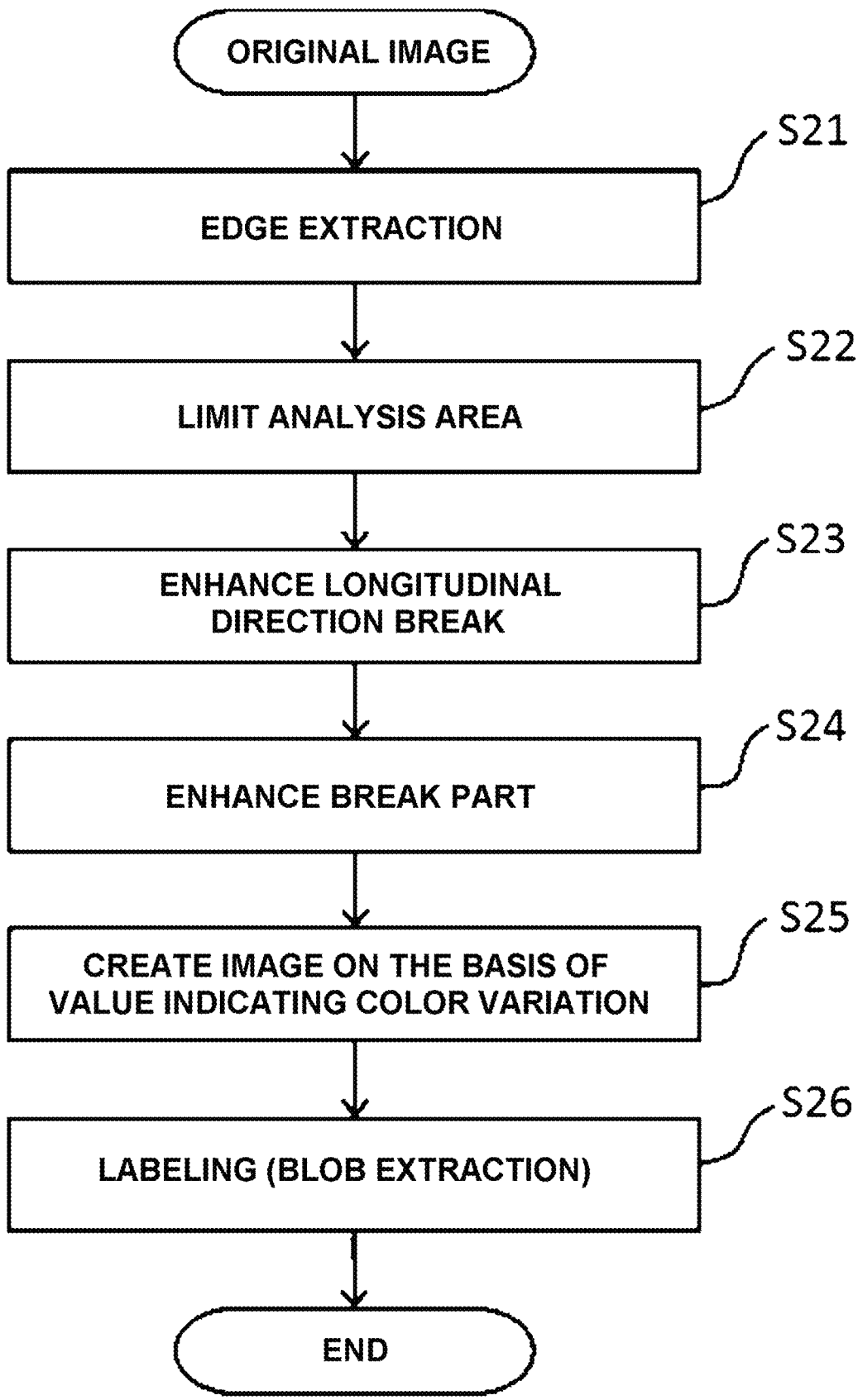

[FIG. 7]
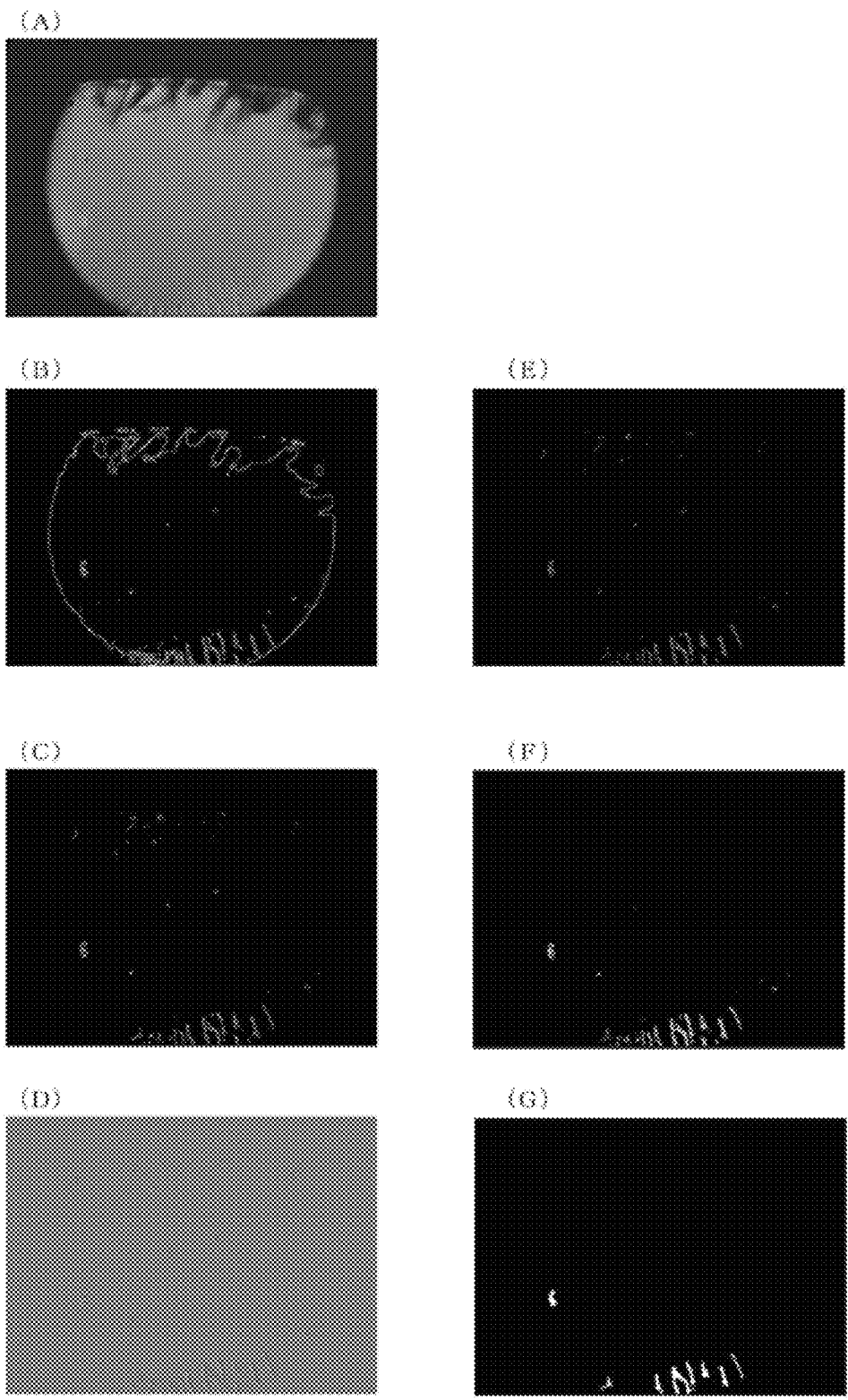

[FIG. 8]
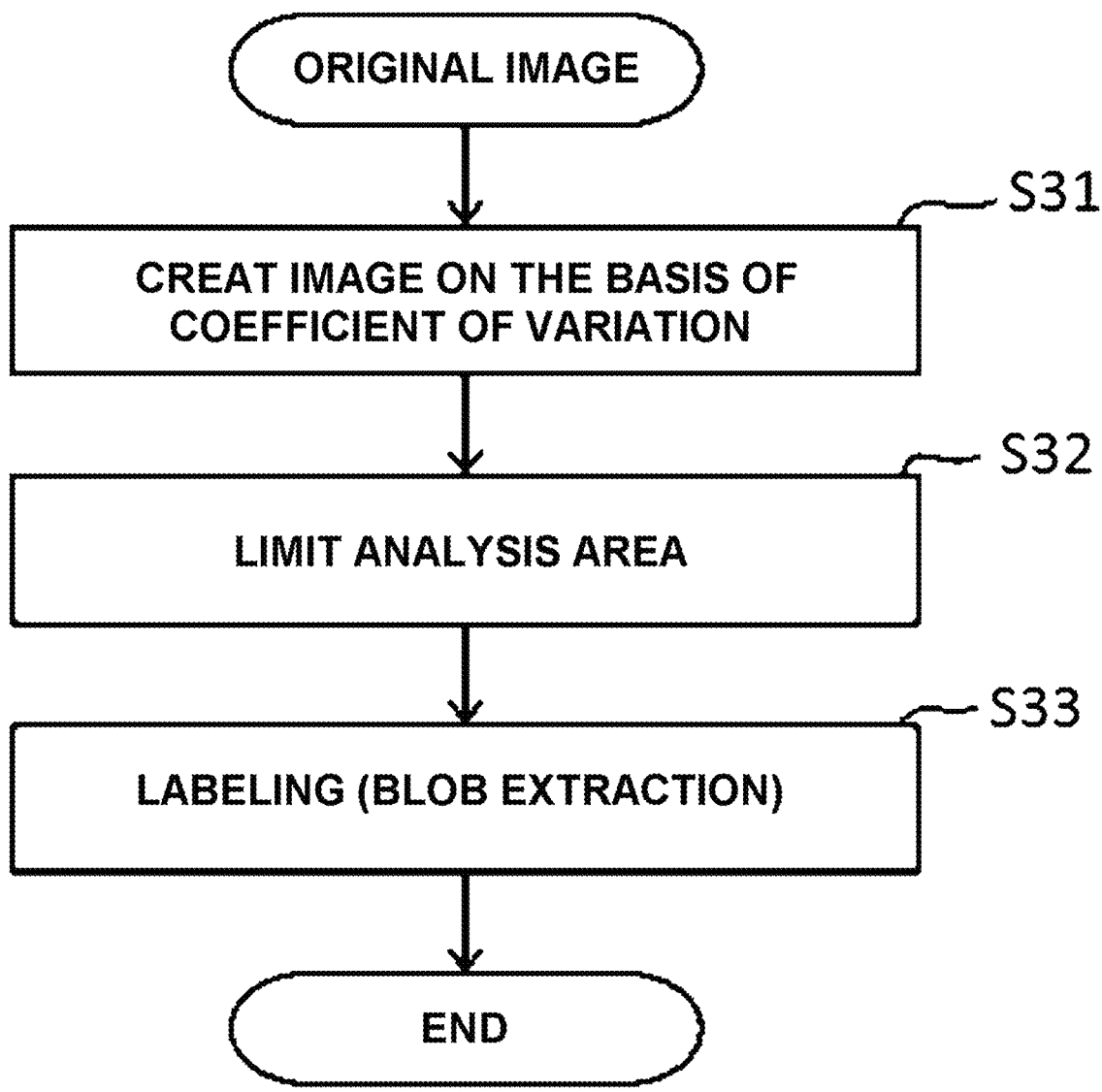

[FIG. 9]
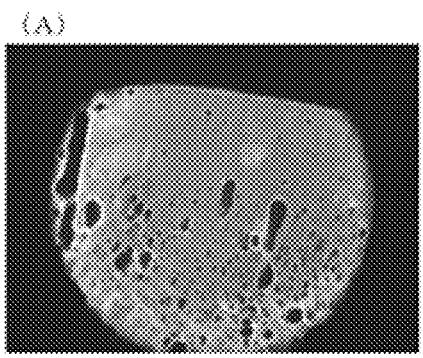
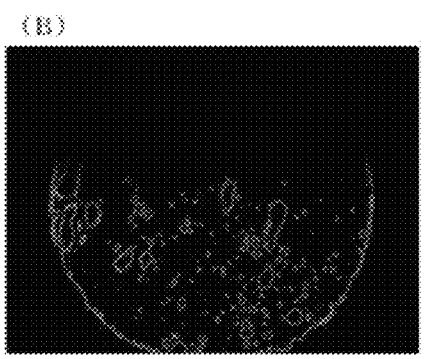
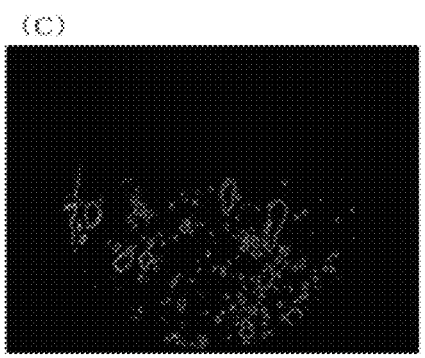
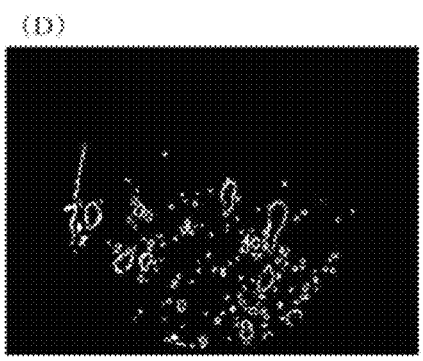

[FIG. 10]
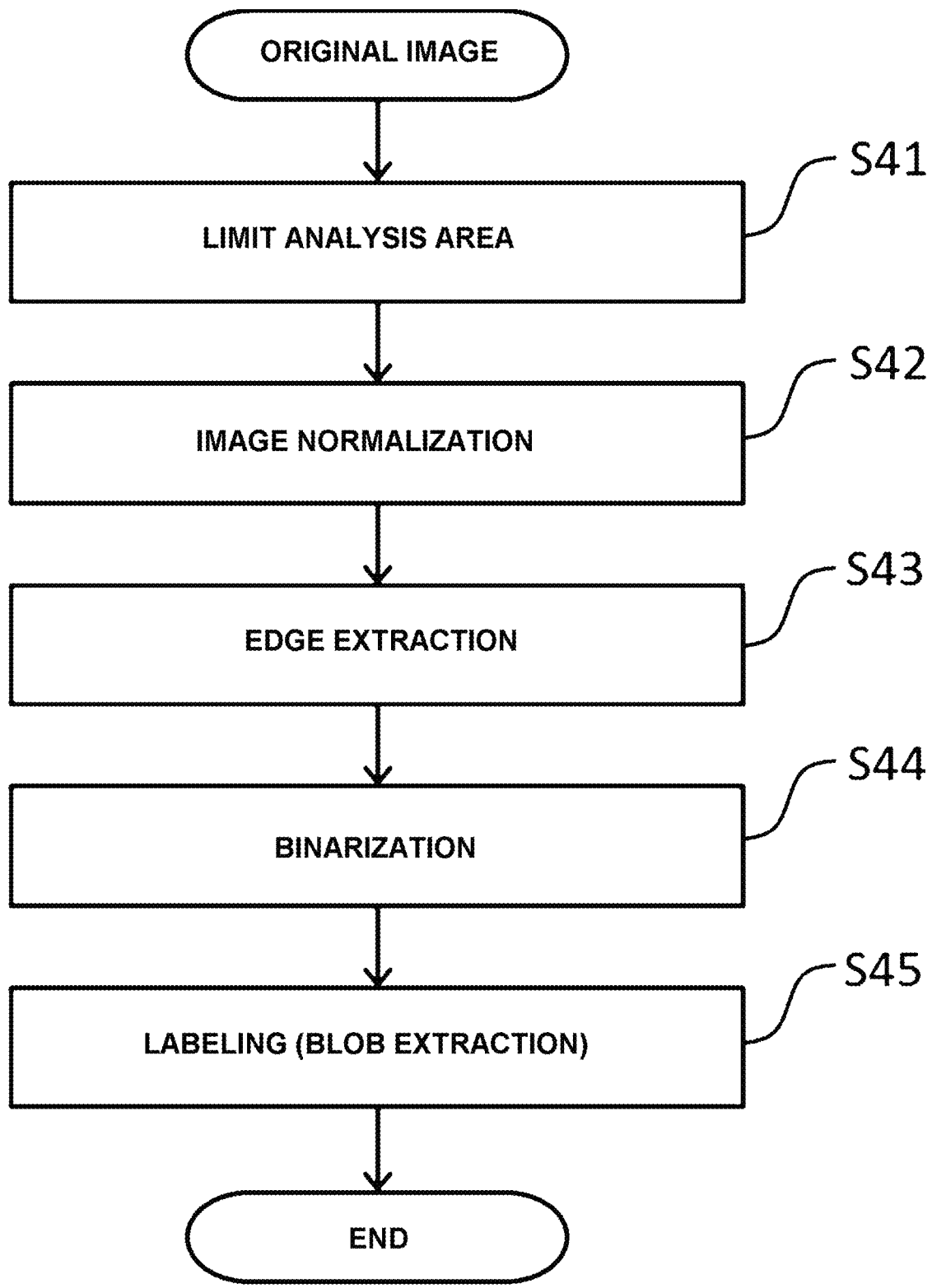

[FIG. 11]
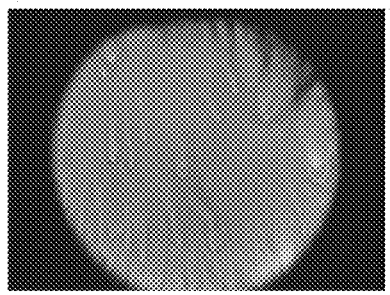
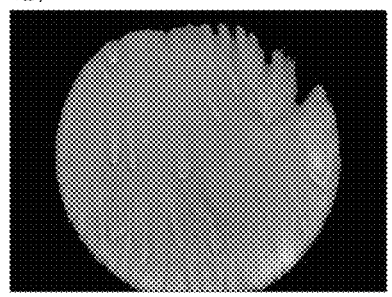
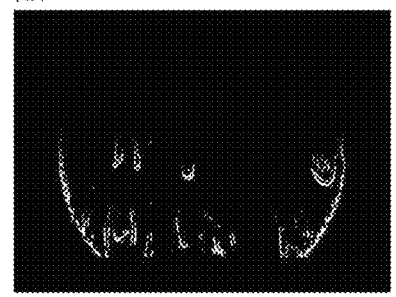
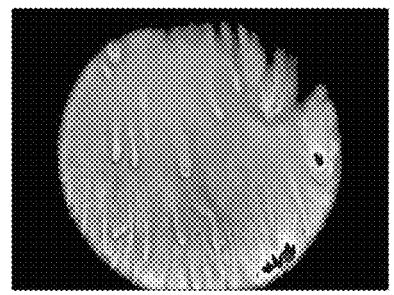
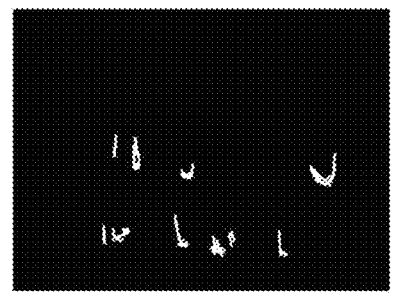
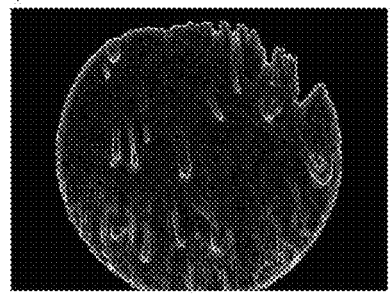

[FIG. 12]
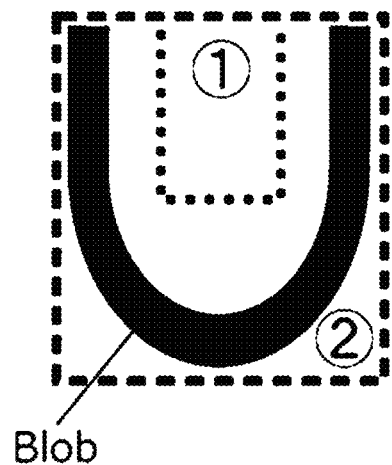
Blob
① SMALL REGION
② RECTANGULAR REGION
---
OCCUPANCY RATIO OF BLOB IN ① IS LESS THAN THRESHOLD VALUE (30%)
⇒ BLOB EXTRACTION

METHOD FOR DYNAMIC EVALUATION OF TEAR FLUID LAYER AND DEVICE THEREFOR

CROSS-REFERENCE OF RELATED APPLICATIONS

This application is the U.S. National Phase under 35 U.S.C. § 371 of International Patent Application No. PCT/JP2018/029860, filed on Aug. 9, 2018, which in turn claims the benefit of Japanese Application No. 2017-155026, filed on Aug. 10, 2017, the entire disclosures of which Applications are incorporated by reference herein.

TECHNICAL FIELD

The present invention relates to a method and a device for dynamically evaluating an interference fringe image of the tear fluid layer, and in particular, a method and a device for evaluating a breaking pattern (breakup pattern) of a tear fluid layer.

BACKGROUND

The eyeball and the eyelid are protected by a tear fluid from entry of a foreign matter, drying, a damage caused by friction, and the like. A tear fluid layer is composed of two layers, a liquid layer including water that occupies most of the tear fluid layer and a glycoprotein (mucin), and a lipid layer covering the liquid layer. The lipid layer prevents evaporation of the water content of the liquid layer by preventing the liquid layer from being in direct contact with the air. A component of the lipid layer is secreted from the meibomian gland present in the eyelid. If the meibomian gland is damaged due to aging, inflammation, scratching, and the like, the lipid layer is not properly formed, causing an ocular disorder, so-called dry eye, due to failure to maintain the liquid layer.

Types of dry eye are classified into an "aqueous tear deficient type," a "short BUT type," an "evaporative type," and a "decreased wettability type." Each of these dry eye types will be outlined. The aqueous tear deficient type is a type in which the secreted tear fluid amount is reduced and the short BUT type is a type in which BUT (Break Up Time), that is, a time between eye opening and breaking of the tear fluid layer, is short. The evaporative type is caused by enhanced evaporation of the tear fluid and the decreased wettability type is caused by a reduction in wettability on the cornea surface. Of these, the evaporative type dry eye and the decreased wettability type dry eye are generally included in the short BUT type.

Regarding this, an ophthalmic apparatus and an image classification method for quantitatively classifying the dry eye types using an interference fringe image of the tear fluid layer are described in Patent Literature 1. According to Patent Literature 1, NIBUT (Non-Invasive Break Up Time) and a lipid layer spread initial speed are measured, and the dry eye types are classified on the basis of a correlation between the NIBUT and the lipid layer spread initial speed. Note that the NIBUT is the BUT which is noninvasively measured without performing staining with a fluorescent dye such as fluorescein.

Patent Literature 1 describes an example in which dry eye can be classified into five types, "aqueous tear deficient dry eye (ATD)," "short BUT type dry eye," "evaporative type dry eye," "post-treatment ATD," and "normal," in accordance with the NIBUT and the lipid layer spread initial speed.

On the other hand, besides the above classification of the dry eye types, such as the aqueous tear deficient type, the short BUT type, the evaporative type, and the decreased wettability type, a breaking pattern (breakup pattern) of the tear fluid layer can be classified on the basis of the dynamics of the tear fluid layer.

Characteristics of the breakup patterns are summarized in FIG. 1. FIG. 1. shows four patterns as the breakup patterns. In FIG. 1, the breakup pattern shown in the leftmost column is a pattern called "area break." The area break is a breakup pattern observed in the aqueous tear deficient dry eye. In this pattern, the breaking of the tear fluid layer appears over a wide range of the cornea at the time of eye opening and the lipid layer spread is not observed, or if any, the lipid layer spread is limited to a lower part of the cornea. This pattern thus has high severity in the aqueous tear deficient dry eye.

Next, in FIG. 1, the breakup pattern shown in the second column from the left is a pattern called "line break." The line break is also a breakup pattern observed in the aqueous tear deficient dry eye. This pattern is characterized in that the breaking of the tear fluid layer appears particularly in a lower part of the cornea during the spreading of the lipid layer, and, further, the breaking appears in a linear shape in the longitudinal direction. Further, in FIG. 1, the breakup pattern shown in the third column from the left is a pattern called "dimple break." The dimple break is one of the breakup patterns observed in the decreased wettability type dry eye of the short BUT type dry eye, and the dimple break is a pattern characterized in that the breaking of the tear fluid layer occurs in a substantially linear shape mainly from a lower part to a center of the cornea during the spreading of the lipid layer.

Further, in FIG. 1, the breakup pattern shown in the rightmost column is a pattern called "spot break." The spot break corresponds to the short BUT type dry eye of the decreased wettability type in which the break often appears in center and upper positions of the cornea at the time of eye opening, and the spot break is a pattern characterized in that the breaking of the tear fluid layer tends to appear in a "substantially circular" shape.

CITATION LIST

Patent Literature

Patent Literature 1: Japanese Patent Application Laid-Open No. 2011-156030

SUMMARY OF INVENTION

Technical Problem

The device and method in Patent Literature 1 could not achieve the dynamic evaluation of the breaking of the tear fluid layer, for example, by evaluating and classifying the breakup patterns on the basis of the process of the breaking of the tear fluid layer.

The present invention has been made in view of the conventional problems described above and provides a device and a method capable of visually and dynamically evaluating an acquired interference fringe image of the tear fluid layer and thereby evaluating and classifying the breakup patterns.

Solution to Problem

The method and device for dynamically evaluating a tear fluid layer according to the present invention include the following steps and means.

(1) The method is a method for dynamically evaluating a tear fluid layer using an interference fringe image of the tear fluid layer composed of a plurality of consecutive frames, the method including: an image creation step of creating at least one break detection image of a first break detection image, a second break detection image, a third break detection image, and a fourth break detection image, which are images for detecting a breaking site of the tear fluid layer; a determination step of determining whether the break detection image created by the image creation step corresponds to a predetermined breakup pattern; a tally step of tallying the determination results determined by the determination step; and an evaluation step of evaluating, on the basis of a tallied result by the tally step, a breakup pattern of the interference fringe image of the tear fluid layer.

(2) In the (1) described above, the image creation step includes, as a step of creating the first break detection image, an edge extraction step of extracting an edge, a longitudinal direction enhancement step of enhancing a break in a longitudinal direction, a step of calculating a value indicating a color variation from color information in a pixel in a predetermined region, an elapsed image step of creating an elapsed image on the basis of the calculated value indicating the color variation, and an extraction step of extracting a connected region of the pixels in the created elapsed image.

(3) In the (1) or (2) described above, the image creation step includes, as a step of creating the second break detection image, an edge extraction step of extracting an edge, a longitudinal direction enhancement step of enhancing a break in a longitudinal direction, a step of enhancing the edge or the break in the longitudinal direction, a step of calculating a value indicating a color variation from color information in a pixel in a predetermined region, an elapsed image step of creating an elapsed image on the basis of the calculated value indicating the color variation, and an extraction step of extracting a connected region of the pixels in the created elapsed image.

(4) In the (1) to (3) described above, the image creation step includes, as a step of creating the third break detection image, a step of calculating a coefficient of variation from color information in a pixel in a predetermined region, a coefficient-of-variation image creation step of creating a coefficient-of-variation image on the basis of the calculated coefficient of variation, and an extracting step of extracting a connected region of the pixels in the coefficient-of-variation image.

(5) In the (1) to (4) described above, the image creation step includes, as a step of creating the fourth break detection image, a normalization step of normalizing an image, an edge extraction step of extracting an edge, a binarization step of performing binarization on the basis of luminance in a pixel, and an extraction step of extracting a connected region of the pixels in the binary image.

(6) In the (1) to (5) described above, the image creation step includes a step of excluding a pixel not requiring analysis through comparison between the color information in the pixel and a threshold value.

(7) In the (2) to (6) described above, the extraction step is a step of extracting the connected region of the pixels satisfying a predetermined condition.

(8) In the (1) to (7) described above, the method includes an eye opening detection step of detecting eye opening in the interference fringe image of the tear fluid layer, and, in the image creation step, the fourth break detection image is created on condition that the frame is in a predetermined time range or a predetermined range of the number of frames from the detection of the eye opening by the eye opening detection step.

(9) In the (1) to (8) described above, in the image creation step, the third break detection image is first created, and it is determined whether creating the other images including the first, second, and fourth break detection images is necessary in accordance with the determination on the created third break detection image in the determination step.

(10) In the (2) to (9) described above, the determination step determines through comparison between at least one of the total number and the total area of the connected regions in the break detection image created by the image creation step and a predetermined threshold value.

(11) In the (1) to (10) described above, the evaluation step evaluates the most frequent breakup pattern as the breakup pattern of the interference fringe image of the tear fluid layer on the basis of the tallied result by the tally step.

(12) In the (1) to (10) described above, the evaluation step evaluates the breakup pattern of the interference fringe image of the tear fluid layer through comparison between an occupancy ratio to the total number of the target frames and a threshold value on the basis of the tallied result by the tally step.

(13) In the (1) to (12) described above, the evaluation step evaluates the breakup pattern with higher severity as the breakup pattern of the interference fringe image of the tear fluid layer on the basis of the tallied result by the tally step.

Advantageous Effects of Invention

According to the present invention, it becomes possible to dynamically and visually grasp a state of the breaking of the tear fluid layer by analyzing the interference fringe image of the tear fluid layer, in particular, a moving image thereof, and, further, it becomes possible to evaluate and classify the breakup patterns from a condition such as the state and the process of the breaking of the tear fluid layer.

BRIEF DESCRIPTION OF DRAWINGS

FIG. 1 is a table summarizing breakup patterns.

FIG. 2 is a schematic diagram illustrating a configuration of an interference fringe image of the tear fluid layer acquiring device.

FIG. 3 is a flow diagram for creating a break detection image 1 for detecting the dimple break in the breakup patterns.

FIG. 4 is an example of images in each step of the creation flow of the break detection image 1.

FIG. 5 is a diagram illustrating an example of color information (luminance value) in each pixel in a part of a target region in an extracted image extracted from an interference fringe image of the tear fluid layer, and a local region for calculating a determination value and a calculation result.

FIG. 6 is a flow diagram for creating a break detection image 2 for detecting the line break in the breakup patterns.

FIG. 7 is an example of images in each step of the creation flow of the break detection image 2.

FIG. 8 is a flow diagram for creating a break detection image 3 for detecting the area break in the breakup patterns.

FIG. 9 is an example of images in each step of the creation flow of the break detection image 3.

FIG. 10 is a flow diagram for creating a break detection image 4 for detecting the spot break in the breakup patterns.

FIG. 11 is an example of images in each step of the creation flow of the break detection image 4.

FIG. 12 is a schematic view conceptually illustrating an example of a condition of Blob extraction in the break detection image 4.

DESCRIPTION OF EMBODIMENTS

Embodiment

Figure 13:
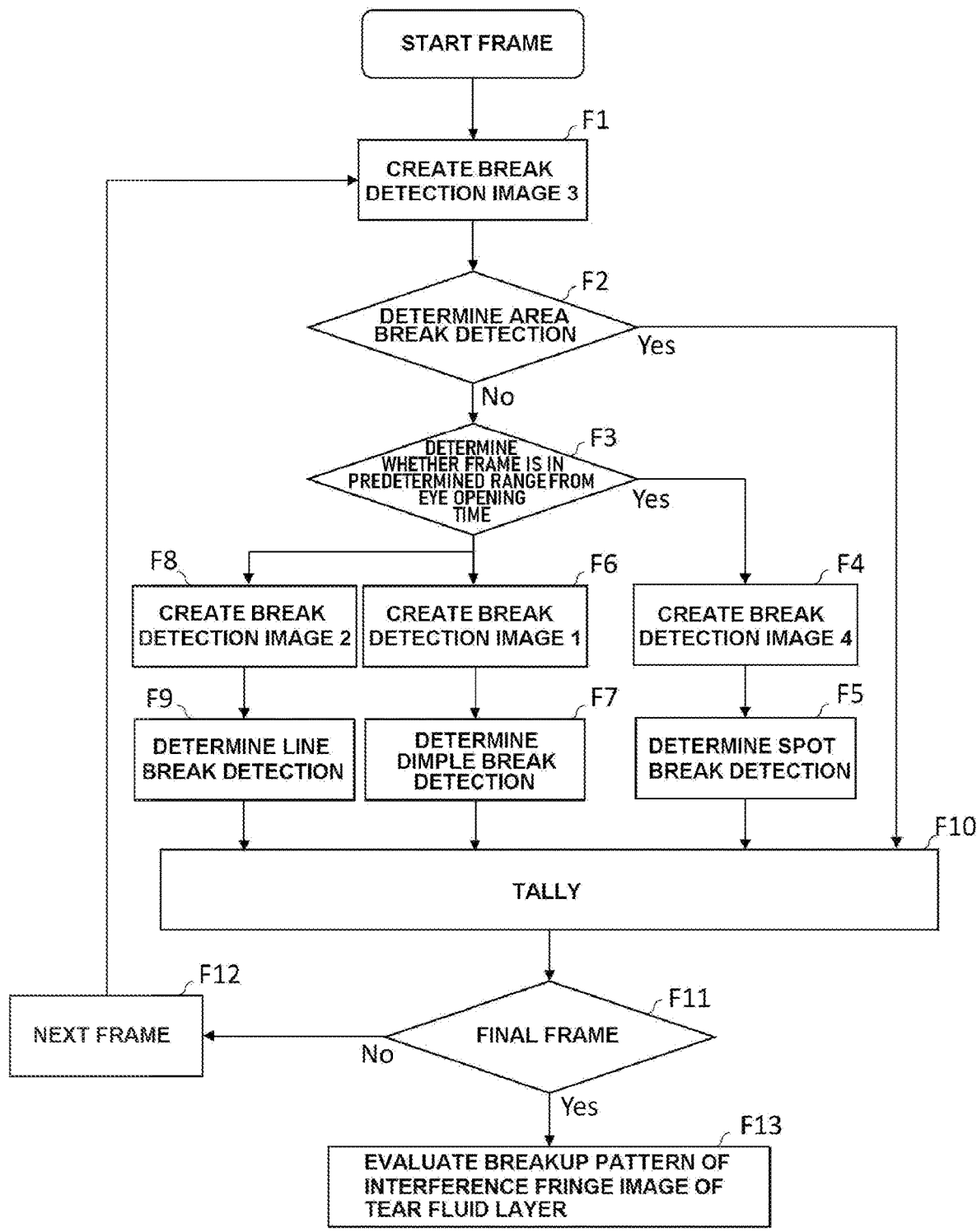
FIG. 13 is a flow diagram until evaluation of the breakup patterns in the interference fringe image of the tear fluid layer.

[Acquisition of the interference fringe image of the tear fluid layer]

As a device for acquiring the interference fringe image of a tear fluid layer on a surface of the cornea (tear fluid layer interference fringe image acquisition device), a conventionally known device may be appropriately used as long as it can record the captured image as digital data. For example, in the tear fluid layer interference fringe image acquisition device schematically shown in FIG. 2, a light beam, which has been emitted from a light source 11 and transmitted through a diaphragm, sequentially passes through a lens 12, a splitter 13, and an objective lens 14 and is condensed on an anterior eye portion 15 of a subject eye of a subject. Reflected light from the anterior eye portion 15 passes through the objective lens 14 and the splitter 13, so that an image is formed on an imaging element 17 via an imaging lens 16. Captured data of the image formed on the imaging element 17 are subjected to predetermined processing by an image processing engine and converted to still image data (hereinafter, simply referred to as "image data") and moving image data.

The tear fluid layer interference fringe image acquisition device is physically or logically connected to a tear fluid layer evaluation device according to the present invention. The tear fluid layer evaluation device includes a processing unit configured to compute and process data and a storing unit configured to store the image data, moving image data, and other data acquired by the tear fluid layer interference fringe image acquisition device. The storing unit stores a computer program and predetermined data for implementing the present invention, while the processing unit processes data according to a predetermined instruction by the computer program and the like.

Processing of the interference fringe image of the tear fluid layer thus obtained for evaluating and classifying a breakup pattern of a dry eye will be described below. Note that, in the following description, unless otherwise specified, the interference fringe images of the tear fluid layer are moving images composed of a plurality of consecutive frames recorded over a predetermined time and stored in a tear fluid layer evaluation device itself or a storage device connected thereto.

[Color Information of Image]

First, the color information usable in the present invention will be described. As an example of a method of using the color information, that of using three color elements of red, green, and blue (numerical values in an RGB color space), which is used in many electronic image apparatuses, is mentioned.

Specifically, the color information in each pixel is luminance or brightness of color elements of red, green, and blue included in the pixel, and the luminance of at least one or more of the color elements of red, green, and blue in the RGB color space may be directly used, or, for example, the luminance may be converted into a gray scale and used.

Further, the color information may be a numerical value obtained by performing an arithmetic operation as necessary. For example, the numerical value may be calculated by combining two or more of the luminance of each of the color elements or by averaging two or more of the color elements. Alternatively, the numerical value may be obtained by multiplying each element by a different predetermined weighting coefficient.

Alternatively, the coefficient of variation may be individually calculated from three color elements of red, green, and blue, and, for example, the maximum value, the minimum value, or the second largest numerical value among them may be used.

The following description will be given on the basis of a case where the luminance in the RGB color space is used, but, as a matter of course, the color information in the present invention is not limited to the numerical values in the RGB color space. As the color information used in the present invention, luminance or brightness defined in the HSV color space, the HSB color space, the HLS color space, the HSL color space, or the like may be used.

Hereinafter, a content of individual processing will be described in detail. In the present invention, creation of break detection images 1 to 4 for detecting the dimple break, the line break, the area break, and the spot break, respectively, will be described. As described below, creation of the break detection images 1 to 4 is performed on a per-frame basis of an interference fringe image of the tear fluid layer. Note that, in the following description, simply referring to "break" basically means the breaking (breakup) of the tear fluid layer.

[Break Detection Image 1]

An acquiring method of the break detection image 1 described herein is particularly for detecting the dimple break, and the procedure thereof is shown in FIG. 3. Note that FIGS. 4 (A) to (F) show an example of photographs in each step of creating the break detection image 1.

<S11: Edge Extraction>

As shown in FIG. 4(A), the dimple break appears in a substantially linear shape over a wide range on the cornea. This break part has appearance in which a white color becomes intense as compared with other parts having no break, thereby causing a change in color information such as luminance between the break part and other parts.

Thus, the break part can be extracted by performing edge extraction that extracts a part having a large change in the color information. As a method of the edge extraction, the Canny method, the first order differentiation method, the Sobel method, the Laplacian method, and the like are conventionally known, and these methods can be appropriately used. In this process, the edge extracted image as shown in FIG. 4(B) can be obtained.

<S12: Limiting Analysis Area>

As shown in FIG. 4(B), in the edge extracted image, the outline of the cornea appears in a circular-arc shape. This is because, in general, a part on the cornea appears brightly and the other parts appear darkly in the interference fringe image of the tear fluid layer, causing the outline of the cornea to be erroneously extracted as the edge.

As shown in FIG. 4(C), the cornea outline part, which is not a site exhibiting the breaking of the tear fluid layer, is desirably excluded not to be included as an object of analysis. The cornea outline part is excluded from the object of analysis, for example, by dynamically recognizing the cornea outline part through the detection of the cornea outline part using a characteristic appearing in the cornea outline part such as a difference in luminance between the cornea and the background. Then, a method in which the color information of the corresponding part thus recognized is changed to the same color information of the background color may be used, or the analysis area may be limited to the inside of the corresponding part recognized as the cornea outline. Further, a conventionally known method can be used in addition to the methods exemplified above. Further, a pixel region possibly causing an adverse effect to the analysis result, for example, a black spot derived from "eyelash" or "oil droplet," captured in the interference fringe image of the tear fluid layer may be excluded in advance.

<S13: Enhancing Longitudinal Direction Break>

The dimple break is characterized by having a linear break in a longitudinal direction, thus processing for enhancing the longitudinal direction break is preferably performed.

For enhancing the break in the longitudinal direction, a difference in the color information such as luminance between a pixel of interest and pixels adjacent thereto in the edge extracted image is used. Specifically, the difference between the color information in a pixel of interest and the color information in pixels adjacent thereto in a lateral direction and the difference between the color information in the pixel of interest and the color information in the pixels adjacent thereto in a longitudinal direction are obtained by scanning, and then a value obtained by subtracting the difference in the longitudinal direction from the difference in the lateral direction is returned as the color information in the pixel of interest, which makes it possible to obtain a longitudinal direction enhanced image (FIG. 4(D)) in which a part that changes in the longitudinal direction is enhanced.

<S14: Creating Image on the Basis of Value Indicating Color Variation>

A value indicating a color variation is calculated on the basis of the color information in the pixels of the longitudinal direction enhanced image obtained as described above, and an image based on the value indicating the color variation is created.

As the color variation, a variance, a deviation (a standard deviation, etc.), or a coefficient of variation, obtained from the color information such as luminance of each color element, can be appropriately used.

The value indicating the color variation is preferably calculated in relation to a local region in which a pixel of interest and pixels adjacent thereto are grouped together. The value indicating the color variation obtained in this manner contributes to specify a position and an area of the break as the resolution is high and spatial position information is matched with that of the original image. The detailed description thereof will be given with reference to FIGS. 5A and B.

FIG. 5A is a schematic diagram in which a standard deviation of the luminance is calculated in a region composed of a total of 9 pixels of 3×3 including a pixel of interest and 8 pixels surrounding the pixel of interest in a target region in an image. Each numerical value in FIG. 5A indicates a numerical value of the color information (luminance) in each pixel in a part of the image obtained as described above.

A "region 1" shown in FIG. 5A is composed of a region composed of a total of 9 pixels (3×3 pixels) including a pixel 1 of interest and pixels surrounding the pixel 1 of interest, and a standard deviation in the region 1 is calculated and outputted to the pixel 1 of interest. FIG. 5B shows a result in which the target region in the image having the color information such as luminance as shown in FIG. 5A is scanned in this manner.

That is, the target region (entire or a desired part) of the image obtained as described above is scanned using a filter for outputting, to the pixel of interest, the value indicating the color variation such as a standard deviation of the color information such as luminance in the local region composed of a pixel of interest and predetermined pixels around the pixel of interest as a center, and the value outputted in each pixel is stored.

Confirming specific numerical values in FIGS. 5A and B, the standard deviation outputted to the pixel 1 of interest in the region 1 is as small as "2.2," while the value outputted to the pixel 2 of interest in the region 2 is as large as "7.1." In principle, the value indicating the color variation tends to be higher in the vicinity of the break where the state of the tear fluid layer is poor.

Note that, in the description above, in FIG. 5, the value indicating the color variation such as a standard deviation in the local region composed of a pixel of interest and pixels surrounding the pixel of interest is outputted to each pixel of interest. However, instead of outputting to the pixel of interest, the local region may be regarded as a section and the value indicating the color variation such as a standard deviation may be outputted to each section. Further, the local region or the section is not limited to the total of 9 pixels of 3×3 and may be a group having any number of the pixels.

As described above, the value indicating the color variation in the break detection image 1 is obtained by calculating a variation, that is, a variance, a standard deviation, or the like, of the color information (luminance, etc.) in the predetermined region.

An image is created on the basis of the value indicating the color variation outputted to each pixel. For example, the value indicating the color variation in each pixel in the image is compared with a predetermined threshold value to extract the pixel having a threshold value or greater, and the extracted pixel is subjected to grayscale processing as the color information (luminance, etc.) in accordance with the value indicating the color variation. Adjustment may be appropriately made such that the luminance is increased as the value indicating the color variation is greater and the luminance is decreased as the value is smaller. Processing may be performed such that the color information of the pixel less than the threshold value is set to zero or set to be same as that of the background color. In this manner, the grayscale image (FIG. 4(E)) which is based on the value indicating the color variation can be acquired.

<S15: Labeling (Blob Extraction)>

The image obtained in the aforementioned steps is subjected to labeling to extract a connected region of the pixels, that is, a "Blob." A labeling method is beyond the scope of the present invention and is not described in detail. However, any method capable of recognizing and extracting a Blob of the pixels having a common logic state may be used, and any conventionally known method can be appropriately used.

Instead of simply extracting a Blob, a noise such as a part irrelevant to the break part may be excluded by comparing the number of the pixels in each Blob extracted by labeling with a predetermined threshold value and extracting only the Blob equal to or greater than the threshold value.

Further, the dimple break is extended in a linear shape and the Blob having a high circularity is likely not to be the break, and thus such a Blob is preferably excluded. The circularity of the Blob is higher as a value calculated by the following "formula 1" is greater. Thus, a threshold value may be set to extract only the Blob having a low circularity.

(Formula 1) Circularity=4π×(number of pixels in Blob)/(perimeter of Blob)²

Further, the dimple break is a linear break, and thus only the Blob appearing in a linear shape may be extracted on the basis of an aspect ratio of the Blob.

Note that the line break described below has a characteristic in common with the dimple break in that the break in a linear shape is extended in the longitudinal direction. On the other hand, the difference is that the length of the dimple break in the longitudinal direction is generally longer than that of the line break and the dimple break is extended not only in the longitudinal direction, but also in the lateral direction.

The break detection image 1 for detecting the dimple break is created by utilizing such a difference. For example, the Blob may be extracted such that the extracted Blob has a length in the longitudinal direction of equal to or greater than a predetermined threshold value, or the Blob having a length in the lateral direction of equal to or greater than a predetermined threshold value may be extracted.

The break detection image 1, for example, as shown in FIG. 4(F), is created in the foregoing steps.

[Break Detection Image 2]

Next, a procedure for creating the break detection image 2 will be described. The break detection image 2 is particularly for detecting the line break. FIG. 6 shows a flow for creating the break detection image 2, and a content of processing in each step will be described below. A creation procedure of the break detection image 2 has many parts common to the creation procedure of the break detection image 1. In the common parts, the processing content is the same as that of the break detection image 1 described above and the descriptions thereof will be omitted as appropriate. FIGS. 7 (A) to (G) show an example of photographs in each step of creating the break detection image 2.

<S21: Edge Extraction>

As shown in FIG. 7(A), the line break appears in a linear shape intensively in a lower part of the cornea, and thus edge extraction is performed by utilizing this characteristic in order to extract a tear fluid layer breaking site. Details thereof are as previously described in "<S11: edge extraction> in Break detection image 1" and an example of an image after the edge extraction is as shown in FIG. 7(B).

<S22: Limiting Analysis Area>

Similar to the break detection image 1, the outline of the cornea appears in a circular-arc shape as shown in FIG. 7(C), and thus processing of excluding the outline of the cornea is performed. Details thereof are as previously described in "<S12: limiting analysis area> in Break detection image 1."

<S23: Enhancing Longitudinal Direction Break>

Similar to the dimple break, the line break is characterized by having a linear break in the longitudinal direction. Thus, a longitudinal direction enhanced image is preferably obtained by performing processing of enhancing the longitudinal direction break. Details thereof are as previously described in "<S13: enhancing longitudinal direction break> in Break detection image 1" and an example of an obtained longitudinal direction enhanced image is as shown in FIG. 7(D).

<S24: Enhancing Break Part (Optional)>

The line break is short in a linear shape as compared with other breakup patterns and the breaking of the tear fluid layer appears in a small range on the cornea, and thus processing of enhancing the breaking part may be performed, although the processing is not essential.

For example, as shown in FIG. 7(E), processing of expanding the edge extracted as described above can be performed. Besides this, a shrinking method, a method of painting out the inside of the extracted edge with predetermined color information, or the like can be used.

<S25: Creating Image on the Basis of Value Indicating Color Variation>

This processing is to create an image (FIG. 7(F)) on the basis of the value indicating the variation of the color information using the image obtained by the processing until "S24" or "S23." Details thereof are as previously described in "<S14: creating image on the basis of value indicating color variation> in Break detection image 1."

<S26 Labeling (Blob Extraction)>

The image obtained in these steps is subjected to labeling to extract a Blob. This method, including the processing of appropriately excluding a noise, is substantially the same as the method previously described in "<S15: labeling (Blob extraction)> in Break detection image 1."

However, the break detection image 2 is an image for detecting the line break, and thus the Blob extraction in the break detection image 2 is performed as follows.

In this processing, the line break is a break extending in a linear shape, and thus the Blob having a high circularity is likely not to be the break. Thus, similar to the aforementioned case of the break detection image 1, such a Blob is desirably excluded. Therefore, only the Blob having a low circularity may be extracted in the same manner described above. Alternatively, only the Blob which can be evaluated as an elongated linear shape may be extracted on the basis of an aspect ratio of the Blob in a similar manner.

However, as described above, the length of the line break in the longitudinal direction tends to be shorter than that of the dimple break in comparison with the dimple break. Thus, for example, among the Blobs which can be evaluated as an elongated linear shape on the basis of the aspect ratio, only the Blob having a length in the longitudinal direction of less than a threshold value may be extracted.

The break detection image 2, for example, as shown in FIG. 7(G), is created in the foregoing steps.

[Break Detection Image 3]

Next, a procedure for creating the break detection image 3 will be described. The break detection image 3 is particularly for detecting the area break. FIG. 8 shows a flow for creating the break detection image 3, and a content of each processing will be described below. Each photograph in FIG. 9 is an example in each step of creating the break detection image 3.

<S31: Creating Image on the Basis of Coefficient of Variation>

As shown in FIG. 9(A), the area break appears over a wide range and shows high severity of dry eye.

The process has been previously described in <S14: creating image on the basis of value indicating color variation> according to "Break detection image 1." Here, instead of using the value indicating the color variation as it is, a value obtained by dividing the value indicating the color variation by an average value of the luminance in the pixels in the region is preferably used. For example, in a case where a standard deviation of the luminance is used as the value indicating the color variation, a coefficient of variation representing that value is given by the "formula 2."

Coefficient of variation=standard deviation of luminance/luminance average value    (Formula 2)

In a case where the subject eye has a severe symptom in which the break is spread in a wide range as seen in the area break that can be diagnosed as dry eye severity grade 5, there are instances where the break cannot be properly determined by using only the numerical value calculated as the variance or the standard deviation of the color information such as luminance described above.

This is because, in a case of severe dry eye where the area break appears, the tear fluid layer breaking site has the constant luminance with less variation as compared with a site where there is no breaking occurring. Thus, if the breaking site of the tear fluid layer is spread in a wide range, there is an increase in the number of sites where the value indicating the variation represented by the variance or the standard deviation described above does not increase, resulting in a risk of failing to properly detect the break or making erroneous determination as a mild symptom which is different from reality.

The coefficient of variation is calculated on the basis of the color information such as luminance in a local region which is composed of a pixel of interest and pixels adjacent thereto, as described in <S14: creating image on the basis of value indicating color variation> in Break detection image 1.

The value indicating the color variation such as a standard deviation of the color information such as luminance in the local region composed of a pixel of interest and predetermined pixels around the pixel of interest as a center is calculated, and an average value of the color information in the pixels in the local region is further calculated. Then, a target region (entire or a desired part) in the interference fringe image of the tear fluid layer is scanned using a filter for outputting a coefficient of variation obtained by dividing the calculated value indicating the color variation by the average value to the pixel of interest to acquire the coefficient of variation in each pixel. Binarization or grayscale processing may be performed on the basis of the coefficient of variation through comparison with a threshold value.

<S32: Limiting Analysis Area>

In the binary image, the outline of the cornea appears in a circular-arc shape as shown in FIG. 9(B). Thus, processing of excluding the arc-shaped part is performed as shown in FIG. 9(C). This processing is the same as that in "<S12: limiting analysis area> in Break detection image 1" described above.

<S33: Labeling (Blob Extraction)>

The binary image obtained as described above is subjected to labeling to extract a Blob. A labeling method is beyond the scope of the present invention and is not described in detail. However, as described above, any conventionally known method capable of extracting connected pixels in the binary image as a Blob can be appropriately used.

Further, as described above, the Blob irrelevant to the break of the area break is desirably excluded. For example, this may be achieved by comparing the number of the pixels in each Blob with a predetermined threshold value and extracting only the Blob equal to or greater than the threshold value.

The break detection image 3, for example, as shown in FIG. 9(D), is created in the foregoing steps.

[Break Detection Image 4]

Next, a procedure for creating the break detection image 4 will be described. The break detection image 4 is particularly for detecting the spot break. FIG. 10 shows a flow for creating the break detection image 4, and a content of each processing will be described below. Each photograph in FIG. 11 shows an original image (FIG. 11(A)) representing an example of an image in which the spot break appears, and an example of images created in each step of creating the break detection image 4 from this original image.

<S41: Limiting Analysis Area>

A step of limiting of an analysis area is the same as previously described in "<S12: limiting analysis area> in Break detection image 1." An example of an image created in this step "<S41: limiting analysis area>" is shown in FIG. 11(B).

In this step, the spot break appears from a center to an upper part on the cornea. Thus, a lower region of the image may be excluded from the analysis area.

<S42: Image Normalization>

The spot break tends to appear in a "substantially circle shape." However, the shape of the spot break varies and a luminance change becomes small as the image brightness varies in each image. Thus, it is sometimes difficult to extract, as an edge, an appearance site of the spot break that is originally desired to be extracted. For example, in a case where an image is dark on the whole, the luminance change between the break appearance site and a site that is not the break appearance site is hardly captured, making it difficult to extract the break appearance site. Further, conversely, in a case where an image is bright on the whole, a site that is not the break appearance site may be erroneously recognized as an edge.

Thus, for the purpose of making the contrast and brightness of the image constant, the image is processed for normalization so that the luminance distribution of the image is within "an average value ±standard deviation." In this process, the original luminance distribution used for the normalization is constituted by a group of the pixels used as an analysis object in the image which has been subjected to the step previously described in <S41: limiting analysis area>.

Specifically, for example, a normal distribution composed of the pixels having luminance of 70 or more is processed to have a luminance distribution of "150±30" after the image normalization. However, the luminance distribution is not limited to this numerical value and the numerical value thereof may be appropriately changed. An example of an image created by this step "<S42: image normalization>" is shown in FIG. 11(C).

<S43: Edge Extraction>

The normalized image thus obtained is subjected to edge extraction. Specifically, for example, in a case of using the "Sobel method," scanning is performed using an appropriately weighted "3×3" horizontal direction differential kernel and vertical direction differential kernel, to extract an edge in the vertical (longitudinal) direction and an edge in the horizontal (lateral) direction, respectively. However, the edge extraction method is not limited thereto, and various methods previously mentioned in "<S11: edge extraction> in Break detection image 1" may be used with modifications. An example of an image created in this step "<S43: edge extraction>" is shown in FIG. 11(D).

<S44: Binarization>

In order to facilitate the detection of the break appearance site, the edge extracted image obtained in the aforementioned manner is subjected to binarization. Specifically, the binarization is performed by setting a threshold value to "100" and comparing this threshold value and the luminance in each pixel. An example of an edge extracted image created in this step "<S44: binarization>" is shown in FIG. 11(E).

<S45: Labeling (Blob Extraction)>

The binary image obtained in the aforementioned "<S44: binarization>" is subjected to the labeling processing to extract a Blob that satisfies a predetermined condition. In order to prevent the extraction of the Blob irrelevant to an appearance site of the break, the Blob of which an area (the number of the pixels) is less than a threshold value is preferably excluded.

In this process, there are a plurality of methods for properly extracting the Blob indicating an appearance site of the spot break. As described above, the spot break has a "substantially circle" shape," and thus one method is configured to keep, among the Blobs having an area (the number of the pixels) of a threshold value or greater, only the Blob having a circularity within a predetermined range. As commonly known, a numerical value calculated by the aforementioned "formula 1" may be used as the circularity, and extraction of the Blob or the necessity of exclusion of the Blob may be determined through comparison between a threshold value and the circularity thus calculated.

Further, besides a "substantially circle shape," the spot break often has a "U"-shape or a longitudinally long shape which may be obtained by elongating a "U" shape longitudinally. Thus, as shown in FIG. 12, a rectangular region that surrounds a Blob is set, and a small rectangular region is further set inside the rectangular region thus set. The small region is set such that only one side of the small region is in contact with a side of the rectangular region.

Specifically, for example, a predetermined side of the rectangular region is defined as a "side 1," and a length equal to one-third of the side 1 can be set to a length of two parallel sides of the small region, while a length equal to one-half of a side orthogonal to the "side 1" of the rectangular region can be set to a length of other two sides of the small region. However, the length of each side of the small region is not limited thereto.

In this configuration, an occupancy ratio of a Blob in the small region set to the Blob is calculated, and, if the ratio is less than a threshold value, the Blob is extracted as the Blob is likely to be a spot break appearance site. On the other hand, if the ratio is equal to or greater than the threshold value, the Blob is excluded as the Blob is likely not to be a spot break appearance site. The threshold value and condition for the ratio of the Blob occupied in the small region are most preferably set to "less than 30%" for a detection result, although the threshold value and condition are not limited thereto.

Further, in order to prevent the detection of the break other than the spot break, for example, the line break and dimple break, the Blob of which an outer peripheral width or a height is equal to or greater than a threshold value may be excluded.

The break detection imagee, for example, as shown in FIG. 11(F), is created in the foregoing steps.

The foregoing paragraphs describe the image creation procedures of four patterns of the break detection images 1 to 4. Hereinafter, procedures until determination and evaluation of the breakup patterns will be described with reference to FIG. 13.

[Interference Fringe Image of the Tear Fluid Layer as Analysis Object]

In the interference fringe image of the tear fluid layer (moving image) as an analysis object, an analysis is performed on a per-frame basis in the moving image. Thus, each frame of the original image in the prepared moving image is sequentially subjected to processing in accordance with the following procedures.

<F1: Creating "Break Detection Image 3">

First, the "break detection image 3" is created in accordance with the steps "S31 to S33" previously described in "Break detection image 3" for detecting the area break.

<F2: Determining Area Break Detection>

After the break detection image 3 is created and the Blob of the pixels is extracted from the break detection image 3, the "total number of Blobs" and the "total area (total number of pixels) of Blobs" are acquired to determine whether the "total number of Blobs" and the "total area of Blobs" satisfy conditions through comparison with predetermined threshold values. For example, in the break detection image 3, the threshold value of the "total number of Blobs" can be set to "less than 20," while the threshold value of the "total area of Blobs" can be set to "5,000 or greater." However, the threshold values and conditions are not necessarily limited thereto and may be appropriately changed.

In "<F2: determining area break detection>," if the "break detection image 3" satisfies the conditions, the detection area break is determined to be detected.

<F3: Determining Whether Frame is in Predetermined Range from Eye Opening Time>

In "<F2: determining area break detection>," if the "break detection image 3" fails to satisfy the conditions, it is further determined whether the frame corresponds to a predetermined frame. Specifically, it is determined whether the frame is from 0.1 seconds to 0.5 seconds after the eye opening. If so, the processing proceeds to "<F4: creating "break detection image 4>" described below.

The procedure, "<F4: creating "break detection image 4>," is for detecting the spot break. The spot break appears immediately after the eye opening, thus, as for the spot break, it is useful to analyze only the frames in a predetermined range after the eye opening.

Further, a method for detecting the eye opening is not particularly limited. For example, the interference fringe image of the tear fluid layer at the eye closing time is in a state where the luminance is significantly low on the whole and the luminance change can be easily determined as compared with that at the eye opening time. Thus, it is determined whether the frame is in a predetermined time range from the eye opening time by detecting the eye opening time through the detection of such a luminance change.

Note that the range of the frames may be set by the order and the number of the frames, for example, the range is set "from the third to fifteenth frames" from the frame in which the eye opening is detected.

<F4: Creating "Break Detection Image 4">

For detecting the spot break, the "break detection image 4" is created in accordance with the steps "S41 to S46" previously described in "Break detection image 4."

<F5: Determining Spot Break Detection>

After the break detection image 4 is created and the Blob is extracted from the break detection image 4, the "total number of Blobs" and the "total area (total number of pixels) of Blobs" are acquired to determine whether the "total number of Blobs" and the "total area of Blobs" satisfy conditions through comparison with predetermined threshold values. For example, in the break detection image 4, the threshold value of the "total number of Blobs" can be set to "less than 20," while the threshold value of the "total area of Blobs" can be set to "less than 125,000." However, the threshold values and conditions are not necessarily limited thereto and may be appropriately changed.

In "<F5: determining area break detection>," if the "break detection image 4" satisfies the conditions, the spot break is determined to be detected.

<F6, F8: Creating "Break Detection Image 1" and "Break Detection Image 2">

The aforementioned "break detection image 1" and "break detection image 2" are created for detecting the "dimple break" and the "line break."

In this process, when the "break detection image 1" and the "break detection image 2" are created, the same original image used for creating one image is also used for creating the other image. This is because the "dimple break" and the "line break" detected by the "break detection image 1" and the "break detection image 2" often appear in the same time, and just because one of these two has been detected does not mean that it is appropriate to dismiss the possibility of the other.

As shown in the flow until "<F6, F8: creating "break detection image 1" and "break detection image 2">," in a case of "failing to detect area break" in "<F2: determining area break detection>" and in a case of "not corresponding" to the "frame in predetermined time range from eye opening time" in "<F3: determining whether frame is in predetermined range from eye opening time>," this frame is used for creating both the "break detection image 1" and the "break detection image 2."

As described above, the same frame is used for creating both the "break detection image 1" and the "break detection image 2." However, these images may be created in any order. Any one of the "break detection image 1" and the "break detection image 2" may be created before the other, or the creation processing may be performed concurrently for both images.

<F7, F9: Determining Dimple Break and Line Break Detection>

The break detection image 1 thus created is subjected to "determining dimple break detection (F7)," while the break detection image 2 thus created is subjected to "determining line break detection (F9)."

In "determining dimple break detection (F7)" using the break detection image 1, after the Blobs are extracted from the break detection image 1, the "total number of Blobs" and the "total area (total number of pixels) of Blobs" are acquired to determine whether the "total number of Blobs" and the "total area of Blobs" satisfy conditions through comparison with predetermined threshold values. For example, in the break detection image 1, the threshold value relating to the "total number of Blobs" can be set to "less than 4," while the threshold value relating to the "total area of Blobs" can be set to "less than 10,000." However, the threshold values and conditions are not limited thereto and may be appropriately changed.

In "determining line break detection (F9)" using the break detection image 2, after the Blobs are extracted from the break detection image 2, the "total number of Blobs" and the "total area (total number of pixels) of Blobs" are acquired to determine whether the "total number of Blobs" and the "total area of Blobs" satisfy conditions through comparison with predetermined threshold values. For example, the threshold value relating to the "total number of Blobs" can be set to "less than 10," while the threshold value relating to the "total area of Blobs" can be set to "less than 7,000." However, the threshold values and conditions are not limited thereto and may be appropriately changed.

If the break detection image 1 satisfies the predetermined conditions, the "dimple break" is determined to be detected. Further, if the break detection image 2 satisfies the predetermined conditions, the "line break" is determined to be detected.

<F10: Tally>

The determination result determined in each frame is tallied. The tallying method is not particularly limited. However, the number may be counted up in accordance with the determination results. For example, an item such as "area break, dimple break, and line break" is provided, and, if the area break is determined in "<F2: determining area break detection>," the number of the area break is added up.

Further, each frame and the determination result of each frame may be stored in association with each other. This makes it possible to confirm which breakup pattern appears in which timing.

Note that the frame in which no pattern is determined in "<F2: determining area break detection>," "<F5: determining spot break detection>," "<F7: determining dimple break detection>," and "<F9: determining line break detection>" may be simply determined to be a "frame not corresponding to any of the breakup patterns." Further, there are additional breakup patterns other than the dimple break, the line break, the area break, and the spot break to be detected by the break detection images 1 to 4. Thus, in the present embodiment, the frame not corresponding to any of these breakup patterns may be further subjected to creation and determination of the break detection image for detecting the breakup pattern different from those detected by the break detection images 1 to 4. The frame in which any breakup pattern is still not detected by the foregoing procedure may be determined to be a frame indicating "being healthy" with no detectable break.

As for the spot break, only "detecting the spot break or not" may be simply stored. Further, the frame in which both the "dimple break" and the "line break" are determined to be detected may be stored such that detection of both the "dimple break" and the "line break" can be recognized.

The aforementioned processing is sequentially performed to each frame ("F11" and "F12" in FIG. 13).

<F13: Evaluating Breakup Pattern in Interference Fringe Image of the Tear Fluid Layer>

On the basis of the tallied result of the breakup patterns determined in each frame as above, a method for evaluating which breakup pattern of the interference fringe image of the tear fluid layer as an analysis object finally corresponds to will be described.

A first method is a method in which, on the basis of the number or the ratio of the frames in the tallied result in the entire interference fringe images of the tear fluid layer (or the entire consecutive frames optionally cut out therefrom), the most frequent breakup pattern is evaluated as the breakup pattern of the interference fringe images of the tear fluid layer.

In the first method, for example, if the tallied result shows that, in the entire interference fringe images of the tear fluid layer (or the entire consecutive frames optionally cut out therefrom) thus analyzed, "91% corresponds to the area break, 0.5% corresponds to the dimple break, and 8.5% corresponds to the line break," the area break having the highest ratio is evaluated as the breakup pattern of the interference fringe images of the tear fluid layer.

A second method is a method in which evaluation is performed through comparison between an appearance ratio of the breakup pattern in the entire interference fringe images of the tear fluid layer (or the entire consecutive frames optionally cut out therefrom) thus analyzed and a predetermined threshold value.

For example, if the threshold value is set to 20% and the detection result shows that, in the entire interference fringe images of the tear fluid layer (or the entire consecutive frames optionally cut out therefrom) thus analyzed, "91% corresponds to the area break, 0.5% corresponds to the dimple break, and 8.5% corresponds to the line break," the breakup pattern having less than the threshold value (20%), that is, the dimple break and the line break, may be excluded, and the area break may be evaluated as the breakup pattern of the interference fringe images of the tear fluid layer.

Further, in the second method, if there are a plurality of corresponding patterns having the threshold value or greater, the corresponding plurality of patterns may be evaluated as the breakup patterns instead of evaluating any one of them as the breakup pattern. Alternatively, if there are a plurality of corresponding breakup patterns having the threshold value or greater, the plurality of breakup patterns may be selected through comparison using another index and evaluated as the breakup pattern. As another index, a detection ratio, severity, or the like can be used. The severity may be set in advance for each breakup pattern.

A third method is a method in which, on the basis of the tallied result in the entire interference fringe images of the tear fluid layer (or the entire consecutive frames optionally cut out therefrom) thus analyzed, the breakup pattern having the higher severity is evaluated as the breakup pattern of the interference fringe images of the tear fluid layer. The severity may be set in advance for each breakup pattern.

Note that the pattern may be evaluated as corresponding to a plurality of the breakup patterns instead of being evaluated as and classified to any one of the breakup patterns. Further, the ratio by the breakup pattern thus tallied may be displayed in a form, such as a graph, that facilitates visual evaluation.

In a case where the tally of the spot break is stored as "detected or not detected," whether the spot break is detected or not may be included in addition to the breakup pattern evaluated by any of the aforementioned methods. Further, in the method in which evaluation is made in accordance with the severity of dry eye, like the third method described above, if the spot break has the highest severity among the detected breakup patterns, the spot break may be evaluated as the breakup pattern of the interference fringe images of the tear fluid layer.

While Examples of the present invention has been described above, it is to be understood that the present invention is not limited to the aforementioned Examples and may be modified and embodied in various aspects.

Four kinds of the creation procedures for the break detection images 1 to 4 have been described. However, it is not always necessary to create all four kinds of the break detection images. One to three kinds of the break detection images may be created. For example, if one kind of the break detection image is created, evaluation of the image is made so as to determine whether a pattern corresponds to the breakup pattern indicated by this one kind of the break detection image. Contents and procedures of the determination, the tally, and the evaluation may be appropriately changed as needed.

Further, for example, for calculating the value indicating the color variation, the original image may be appropriately magnified or reduced. As a magnification method, a method in which a gap of the luminance in the pixels is interpolated by a function, such as a bilinear method, a bicubic method, or the Lanczos method, is preferable. As an effect of magnification, a state of the site can be acquired in more detail. On the other hand, as a reduction method, any method including a nearest-neighbor method, a bilinear method, a bicubic method, or the Lanczos method may be used. As an effect of reduction, shortening of analysis time is mentioned. These methods may be selectively used according to the need.

In the aforementioned description relating to the "break detection images 1 and 2," as the order of processing, "edge extraction" is performed prior to performing "enhancing longitudinal direction break." This order can be exchangeable. That is, "edge extraction" may be performed after "enhancing longitudinal direction break."

Regarding creation of the break detection images 1 to 4 in the aforementioned description, each step of "limiting analysis area" and "labeling (Blob extraction)" is performed in any image creation. However, a specific content of the processing is not limited to the aforementioned description. In the aforementioned description, the cornea outline part or the like not requiring analysis is excluded in the step of "limiting analysis area." However, the cornea outline part or the like not requiring analysis may only be specified in the step of "limiting analysis area" and the Blob corresponding to the specified part not requiring analysis may be determined not to be extracted in the step of "labeling (Blob extraction)."

In the aforementioned description, as a condition relating to the threshold value, the terms such as "equal to or less than," "equal to or greater than," and "less than" are used for the convenience of description. However, the condition relating to the threshold value is not limited in accordance with the description. Any threshold value can be used as long as correspondence or non-correspondence can be determined through comparison between a certain value in the interference fringe image of the tear fluid layer and the threshold value.

INDUSTRIAL APPLICABILITY

The present invention enables an objective, non-invasive and efficient evaluation of a breakup pattern, particularly for dry eye subtype diagnosis using interference fringe images of the tear fluid layer.

The invention claimed is:

1. A method for dynamically evaluating a tear fluid layer using an interference fringe image of the tear fluid layer composed of a plurality of consecutive frames, the method being performed using a processing unit of a tear fluid layer evaluation device that is configured to perform:
   an image creation step of creating at least one break detection image of a first break detection image, a second break detection image, a third break detection image, and a fourth break detection image, which are images for detecting a breaking site of the tear fluid layer;
   a determination step of determining whether the at least one break detection image created by the image creation step corresponds to a predetermined breakup pattern;
   a tally step of tallying determination results determined by the determination step; and
   an evaluation step of evaluating, on a basis of a tallied result by the tally step, a breakup pattern of the interference fringe image of the tear fluid layer, the evaluation step corresponds to anyone of,
      (a) the evaluation step is to evaluate a most frequent breakup pattern as the breakup pattern of the interference fringe image of the tear fluid layer, or (b) in case a plurality of breakup patterns are detected, the evaluation step comprises:
comparing between a value (A) and a threshold value, evaluating breakup patterns of which the value (A) is equal to or higher than the threshold value as the breakup pattern of the interference fringe image of the tear fluid layer, wherein the value (A) is an occupancy ratio of frame number of each kind of breakup pattern to a total number of a target frames, and
(c) in case a plurality of breakup patterns are detected, the evaluation step evaluates the breakup pattern with a higher severity as the breakup pattern of the interference fringe image of the tear fluid layer.

2. The method for dynamically evaluating a tear fluid layer according to claim 1, wherein
the image creation step includes, as a step of creating the first break detection image,
an edge extraction step of extracting an edge,
a longitudinal direction enhancement step of enhancing a break in a longitudinal direction,
a step of calculating a value indicating a color variation from color information in a pixel in a predetermined region,
a pixel extraction step to extract pixels of which the value indicating the color variation is equal to or greater than a threshold, and
a connected region extraction step of extracting a connected region of the pixels in the created elapsed image.

3. The method for dynamically evaluating a tear fluid layer according to claim 2, wherein the connected region extraction step is a step of extracting the connected region of the pixels satisfying a predetermined condition in accordance with the first to fourth break detection images.

4. The method for dynamically evaluating a tear fluid layer according to claim 2, wherein the determination step is a step of determining through comparison between at least one of a total number and a total area of the connected regions in the break detection image created by the image creation step and a predetermined threshold value.

5. The method for dynamically evaluating a tear fluid layer according to claim 1, wherein
the image creation step includes, as a step of creating the second break detection image,
an edge extraction step of extracting an edge,
a longitudinal direction enhancement step of enhancing a break in a longitudinal direction,
a step of enhancing the edge or the break in the longitudinal direction,
a step of calculating a value indicating a color variation from color information in a pixel in a predetermined region,
a pixel extraction step to extract pixels of which the value indicating the color variation is equal to or greater than threshold, and
a connected region extraction step of extracting a connected region of the pixels in the created elapsed image.

6. The method for dynamically evaluating a tear fluid layer according to claim 5, wherein the connected region extraction step is a step of extracting the connected region of the pixels satisfying a predetermined condition in accordance with the first to fourth break detection images.

7. The method for dynamically evaluating a tear fluid layer according to claim 5, wherein the determination step is a step of determining through comparison between at least one of a total number and a total area of the connected regions in the break detection image created by the image creation step and a predetermined threshold value.

8. The method for dynamically evaluating a tear fluid layer according to claim 1, wherein
the image creation step includes, as a step of creating the third break detection image,
a step of calculating a coefficient of variation from color information in a pixel in a predetermined region,
a coefficient-of-variation image creation step of creating a coefficient-of-variation image on a basis of the calculated coefficient of variation, and
an extracting step of extracting a connected region of the pixels in the coefficient-of-variation image.

9. The method for dynamically evaluating a tear fluid layer according to claim 8, wherein the connected region extraction step is a step of extracting the connected region of the pixels satisfying a predetermined condition in accordance with the first to fourth break detection images.

10. The method for dynamically evaluating a tear fluid layer according to claim 8, wherein the determination step is a step of determining through comparison between at least one of a total number and a total area of the connected regions in the break detection image created by the image creation step and a predetermined threshold value.

11. The method for dynamically evaluating a tear fluid layer according to claim 1, wherein
the image creation step includes, as a step of creating the fourth break detection image,
a normalization step of normalizing an image,
an edge extraction step of extracting an edge,
a binarization step of performing binarization on a basis of luminance in a pixel, and
an extraction step of extracting a connected region of the pixels in the binary image.

12. The method for dynamically evaluating a tear fluid layer according to claim 11, wherein the connected region extraction step is a step of extracting the connected region of the pixels satisfying a predetermined condition in accordance with the first to fourth break detection images.

13. The method for dynamically evaluating a tear fluid layer according to claim 11, wherein the determination step is a step of determining through comparison between at least one of a total number and a total area of the connected regions in the break detection image created by the image creation step and a predetermined threshold value.

14. The method for dynamically evaluating a tear fluid layer according to claim 1, wherein the image creation step includes a step of excluding a pixel not requiring analysis through comparison between the color information in the pixel and a threshold value.

15. The method for dynamically evaluating a tear fluid layer according to claim 1, wherein the processing unit of the tear fluid layer evaluation device is further configured to perform an eye opening detection step of detecting eye opening in the interference fringe image of the tear fluid layer, wherein
in the image creation step, the fourth break detection image is created on condition that a frame is in a predetermined time range or a predetermined range of number of frames from the detection of the eye opening by the eye opening detection step.

16. The method for dynamically evaluating a tear fluid layer according to claim 1, wherein
in the image creation step, the third break detection image is first created, and
it is determined whether creating the other images including the first, second, and fourth break detection images is necessary in accordance with the determination on the created third break detection image in the determination step.

17. A tear fluid layer evaluation device configured to execute the method according to claim 1.

* * * * *